(12) United States Patent
Bergau et al.

(10) Patent No.: US 12,392,719 B2
(45) Date of Patent: Aug. 19, 2025

(54) DEVICE FOR DETECTING A GAS OR A MULTICOMPONENT GAS MIXTURE

(71) Applicant: Endress+Hauser Group Services AG, Reinach (CH)

(72) Inventors: Max Bergau, Freiburg (DE); Benjamin Scherer, Oberried (DE)

(73) Assignee: Endress+Hauser Group Services AG, Reinach (CH)

( * ) Notice: Subject to any disclaimer, the term of this patent is extended or adjusted under 35 U.S.C. 154(b) by 298 days.

(21) Appl. No.: 18/060,046

(22) Filed: Nov. 30, 2022

(65) Prior Publication Data

US 2023/0204505 A1 Jun. 29, 2023

(30) Foreign Application Priority Data

Dec. 2, 2021 (DE) ...................... 10 2021 131 832.7

(51) Int. Cl.
*G01N 21/39* (2006.01)
*G01N 21/33* (2006.01)
(Continued)

(52) U.S. Cl.
CPC ......... *G01N 21/39* (2013.01); *G01N 33/0004* (2013.01); *G01N 33/0027* (2013.01);
(Continued)

(58) Field of Classification Search
CPC ............... G01N 21/39; G01N 33/0004; G01N 33/0027; G01N 21/33; G01N 21/359; G01N 2021/3513; G01N 2021/399
See application file for complete search history.

(56) References Cited

U.S. PATENT DOCUMENTS 5,430,293 A * 7/1995 Sato ..................... G01M 3/38
250/338.5
8,502,152 B1 8/2013 Hashmonay et al.
(Continued)

FOREIGN PATENT DOCUMENTS

CN 111537157 A 8/2020
DE 112011103665 B4 10/2022

OTHER PUBLICATIONS

Bonow, G., et al., For the automated inspection of plants by means of gas telemetry; technologies and devices, Automation 2011, Jun. 28-29, 2011, Baden-Baden, Germany.
(Continued)

*Primary Examiner* — Dominic J Bologna
(74) *Attorney, Agent, or Firm* — Gil M. Repa; Endress+Hauser (USA) Holding, Inc.

(57) ABSTRACT

A device for detection of a gas or of a multi-component gas mixture comprises: an optical capture unit for capturing a field of view; a first light source configured to emit light having a current wavelength within a first wavelength range, wherein the first light source is arranged such that the light emitted impinges on the field of view; a first optical filter arranged between the optical capture unit and the first light source, wherein the first optical filter enables only those wavelengths of the light in a first filter wavelength range to pass; and a control/evaluation unit configured to determine, based on at least one image recorded by the optical capture unit, the distribution of the gas or the gas mixture in the field of view, the composition of the gas or the gas mixture, and/or a concentration of the components of the gas mixture.

19 Claims, 2 Drawing Sheets

(51) Int. Cl.
*G01N 21/3504* (2014.01)
*G01N 21/359* (2014.01)
*G01N 33/00* (2006.01)

(52) U.S. Cl.
CPC ..... *G01N 21/33* (2013.01); *G01N 2021/3513* (2013.01); *G01N 21/359* (2013.01); *G01N 2021/399* (2013.01)

(56) References Cited

U.S. PATENT DOCUMENTS

| | | | | |
|---|---|---|---|---|
| 2008/0259318 | A1* | 10/2008 | Pan | G01J 3/02 |
| | | | | 356/73 |
| 2009/0159798 | A1 | 6/2009 | Weida et al. | |
| 2013/0229658 | A1* | 9/2013 | Jouanique-Dubuis | |
| | | | | G01N 21/39 |
| | | | | 356/437 |
| 2016/0169740 | A1* | 6/2016 | Jiang | G01N 21/1702 |
| | | | | 356/407 |
| 2019/0172192 | A1 | 6/2019 | Schmidt et al. | |
| 2019/0376890 | A1 | 12/2019 | Bennett et al. | |
| 2020/0363327 | A1* | 11/2020 | Cox | G01M 3/002 |
| 2023/0137550 | A1* | 5/2023 | Kim | G01N 21/6452 |
| | | | | 250/458.1 |
| 2023/0314266 | A1* | 10/2023 | Kreitinger | G01M 3/38 |
| | | | | 356/437 |

OTHER PUBLICATIONS

Nutt, K.J., et al., Developing a portable gas imaging camera using highly tunable active-illumination and computer vision, Optics Express, vol. 28, No. 13, Jun. 22, 2020, https://doi.org/10.1364/OE.389634.

Strahl, Thomas, et al., Methane leak detection by tunable laser spectroscopy and mid-infrared imaging, Applied Optics, vol. 60, No. 15, May 2021, https://doi.org/10.1364/AO.419942.

Wang, Jingfan, et al., Machine vision for natural gas methane emission detection using an infrared camera, Applied Energy, vol. 257(c), 2020, Elsevier, Amsterdam and New York.

* cited by examiner

DEVICE FOR DETECTING A GAS OR A MULTICOMPONENT GAS MIXTURE

CROSS-REFERENCE TO RELATED APPLICATIONS

The present application is related to and claims the priority benefit of German Patent Application No. 10 2021 131 832.7, filed on Dec. 2, 2021, the entire contents of which are incorporated herein by reference.

TECHNICAL FIELD

The invention relates to a device for detection of a gas or of a multi-component gas mixture. Furthermore, the invention relates to a method for detection of a gas or of a multi-component gas mixture by means of a device according to the invention.

BACKGROUND

An emerging trend in gas detection is the detection of gases from a distance. For this purpose, there are what are known as point sensors and gas cameras, wherein the former measure only the gas concentration along a line, while gas cameras provide an image representation of the gas cloud (cf. the publications, Bonow, G.; Kroll, A., "Zur automatisierten Inspektion von Anlagen mittels Gasfernmesstechnik: Technologien and Geräte," AUTOMATION 2011, Baden-Baden, Jun. 28-29, 2011, and Strahl et al., "Methane leak detection by tunable laser spectroscopy and mid-infrared imaging," Appl. Opt. 60, C68-C71 (2021)). The gas cameras are often referred to as optical gas imaging (OGI).

For this purpose, two technologies are established nowadays, which differ in terms of their mode of operation: passive detection and active detection.

Passive detection is the current standard method for gas cameras for detecting gas from a distance. Thermal background radiation, i.e., infrared radiation, is captured by an infrared camera that is normally equipped with a bandpass filter. The filter is selected such that it lets infrared light through only in the vicinity of the absorption lines of the sought gas. If gas is present, the image is "darkened" or "lightened" at these locations, depending upon the temperature of the gas and of the background.

A further comparison, e.g., with a reference image, i.e., with an image entirely without a filter or with a filter, which does not lie on the absorption lines of the target gas, shows the detected gas more clearly. Leading industrial companies selling such products are the former Rebellion Photonics (now Honeywell) and FLIR.

In the case of active detection, instead of using the thermal background radiation, a separate light source is used to illuminate the region of interest. The light transmitted in is reflected by a background, which is required for the functioning of this technique.

Subsequently, the reflected light is evaluated in the same way as in passive detection, i.e., the light intensity on and next to the absorption line is compared. Leading industrial companies are: Sewerin and QLM. Up until now, this technology was only available as point sensors. An example of such an active detection can be found in the publication, K. J. Nutt, N. Hempler, G. T. Maker, G. P. A. Malcolm, M. J. Padgett, and G. M. Gibson, "Developing a portable gas imaging camera using highly tunable active-illumination and computer vision," Opt. Express 28, 18566-18576 (2020).

Both technologies have advantages and disadvantages. The maximum possible measurement distance between the camera and the gas during passive detection can be several hundred meters, whereas it is substantially less during active detection (approximately 2 m).

During passive detection, no requirements are imposed upon the background, while the background must be in the measurement range during active detection.

With regard to the temperature difference, no requirements are imposed during active detection, while the temperature of the gas and the background must differ during passive detection.

With regard to the quantity of gas, no requirements are imposed during active detection, wherein, for passive detection, it must be taken into consideration that, if the gas covers the entire field of view, it cannot be detected.

During active detection, the detected gas can be clearly identified, wherein, during passive detection, typically only the gas group can be detected. The sensitivity during active detection is approximately 1 ppm*m for methane, and, during passive detection, approximately 100 ppm*m for methane.

In methods also differ in detecting the presence of gas. During active detection, the gas is identified as such, while, during passive detection, algorithms are required for this purpose. An example of the latter is described in the publication, Wang et al., 2020, "Machine vision for natural gas methane emissions detection using an infrared camera," Applied Energy, Elsevier, vol. 257(C), in which a deep learning algorithm is used to detect gas clouds in a passive gas camera (OGI).

SUMMARY

Proceeding from the described problem, the object of the invention is to improve the accuracy and selectivity of detection of a gas or of a gas mixture, compared to the passive detection method.

The object is achieved by a device for detection of a gas or of a multi-component gas mixture, wherein the device comprises: an optical capture unit for capturing a field of view of the optical capture unit; a first light source designed to emit light having a current wavelength that can be set within a first wavelength range, wherein the first light source can be selectively switched on and off, and said light source is arranged in relation to the optical capture unit in such a way that the light emitted by the first light source impinges on the field of view of the optical capture unit; a first optical filter arranged in the field of view of the optical capture unit and between the optical capture unit and the first light source, wherein the first optical filter can be in particular selectively connected and disconnected, and wherein the first optical filter lets through only the wavelengths of the light lie first filter wavelength range, wherein the first wavelength range of the first illumination source is located within the first filter wavelength range; and a control/evaluation unit, which is designed to determine, on the basis of the at least one image recorded by the optical capture unit, the presence of the gas or the gas mixture, the distribution of the gas or the gas mixture in the field of view of the optical capture unit, the composition of the gas or the gas mixture, and/or a concentration of the components of the gas mixture.

The device according to the invention combines the advantages of active and passive gas detection in one measuring device. From the perspective of the hardware, this combination is achieved by expanding the optical capture unit to include a suitable, tunable first light source.

The optical capture unit is, for example, a photo or video camera. However, a photodiode (single pixel) or a line detector can also be used. These sensors continuously perform a scan by changing the detection range (photo diode: row-by-row and column-by-column; row detector: row-by-row) in order to be able to capture the entire field of view.

According to an advantageous embodiment of the device according to the invention, it is provided that the control/evaluation unit be designed to synchronize a setting of at least one current wavelength of the first light source with a triggering of the optical capture unit to record at least one image. The optical capture unit is therefore instructed to record an image exactly at the moment when the first light source is switched to the new wavelength.

According to an alternative advantageous embodiment of the device according to the invention, it is provided that the control/evaluation unit be designed to set the light source successively to at least two current wavelengths that differ from one another, wherein the light source is designed to trigger the optical capture unit in each case when the light source is set accordingly to the respective current wavelengths. In this way, an absorption line of the gas or gas mixture to be analyzed or detected can be recorded. Further properties of the gas or of the gas mixture can be determined on the basis of this absorption line.

In a development of the device according to the invention, one or more further optical filters are provided, wherein the further optical filters each have a further filter wave range different from one another and from the first filter wave range.

According to a first variant, it is provided that the device comprise a filter wheel which has the first optical filter and the further optical filter or filters, wherein the filter wheel is designed to selectively arrange the first optical filter, one of the further optical filters, or no optical filter in the field of view of the optical capture unit by rotating the filter wheel.

According to a first variant, it is provided that the device have a filter holder for arranging an optical filter in the field of view of the optical capture unit, wherein, selectively, the first optical filter, one of the further optical filters, or no optical filter can be arranged in the filter holder. The filter holder is located directly in front of the optical capture unit, or in the optical capture unit, e.g., between the objective and the photo sensor, in the event that a camera is used.

An advantageous embodiment of the device according to the invention provides that the first wavelength range of the first light source be narrowband. The wavelength range of a light source is referred to as narrowband when the light source has a full width at half maximum (FWHM) of less than 5 wave numbers.

According to an advantageous embodiment of the device according to the invention, it is provided that the first wavelength range be in the infrared range or in the UV range.

According to an advantageous embodiment of the device according to the invention, it is provided that one or more further light sources be provided, wherein the further light sources each have a further wavelength range different from one another and from the first wavelength range, wherein the further light source, or one of the further light sources, can be selectively switched on and off, and said light source, or the optical capture unit, is arranged such that its emitted light impinges on the field of view of the optical capture unit. The first light source is oriented such that the emitted light impinges on a reflective background, wherein the reflected light is captured by the optical capture unit. In this case, the gas to be analyzed is located in the beam path of the emitted light and/or of the reflected light.

According to an advantageous embodiment of the device according to the invention, it is provided that the first light source, or the further light sources, be a tunable laser, and in particular a diode laser or a quantum cascade laser.

According to an advantageous embodiment of the device according to the invention, it is provided that an optical manipulation unit be provided, which is designed such that it widens the light emitted by the first light source or from the further light source or from one of the further light sources in such a way that said light impinges on the complete field of view of the optical capture unit, or which is designed such that the light emitted by the first light source is present in a punctiform manner and travels in a raster pattern over the field of view of the optical capture unit, wherein the control/evaluation unit is designed to record a plurality of images at different positions of the light in the raster. Complete capture of the field of view of the optical capture unit can be realized by means of both methods.

Furthermore, the object is achieved by a method for detection of a gas or of a multi-component gas mixture by means of a device according to the invention, comprising:
operating the device in a passive detection mode, wherein the first light source is switched off in the passive detection mode, and the optical capture unit captures a first image,
evaluating the captured first image and determining the position of a gas or a gas mixture in the field of view of the optical capture unit,
operating the device in an active detection mode, wherein the first light source is switched on in the active detection mode and emits light having a first current wavelength:
  i. directing the device with the optical capture unit towards the determined position and capturing a second image by means of the optical capture unit;
  ii. capturing a third image by means of the optical capture unit at the same position, wherein the first light source emits a second current wavelength different from the first current wavelength,
determining the composition of the gas or the gas mixture, or identifying the gas or the gas mixture, by evaluating the second image and the third image.

According to the invention, the position of the gas or the gas mixture is thus first determined, and then, in the active detection mode, properties of the detected gas or gas mixture are determined. It is provided here that the first current wavelength be sufficiently distant from the wavelength which is maximally absorbed by the gas or the gas mixture, such that no absorption or reduced absorption (for example, 10% of the maximum absorption) of the light emitted by the first light source occurs under normal conditions. The second image captured in this way is used as a reference image. The second current wavelength is selected such that, under normal conditions, maximum absorption of the light emitted by the first light source through the gas or the gas mixture occurs. The captured third image is compared with the reference image by image differencing, and the properties of the gas or of the gas mixture are determined by evaluating or comparing both images.

According to an advantageous embodiment of the method according to the invention, it is provided that the light source emit the first current wavelength and one or more further current wavelengths one after another, wherein the optical capture unit records at least one further image when each of the further current wavelengths is present, wherein the further image or the further images are also evaluated to determine the composition of the gas or the gas mixture, or to identify the gas or the gas mixture. What is known as a "sweep" of the first light source is thus performed. As a result, a spectral line of the gas or of the gas mixture is recorded, on the basis of which the properties of the gas or of the gas mixture can be determined.

According to an advantageous embodiment of the method according to the invention, it is provided that the one or more of the further light sources be subsequently successively switched on, wherein in particular several current wavelengths are set one after another, and wherein the optical capture unit records one or more further current images, wherein the further image or the further images are also evaluated to determine the composition of the gas or the gas mixture, or to identify the gas or the gas mixture.

According to an advantageous embodiment of the method according to the invention, it is provided that one of the further optical filters be connected for each of the further light sources. It is provided here that the respective wavelength ranges of the further light sources lie in the filter wavelength ranges of the respectively corresponding further optical filter.

The invention is explained in greater detail with reference to the following figure. Illustrated are:

DETAILED DESCRIPTION

Figure 1:
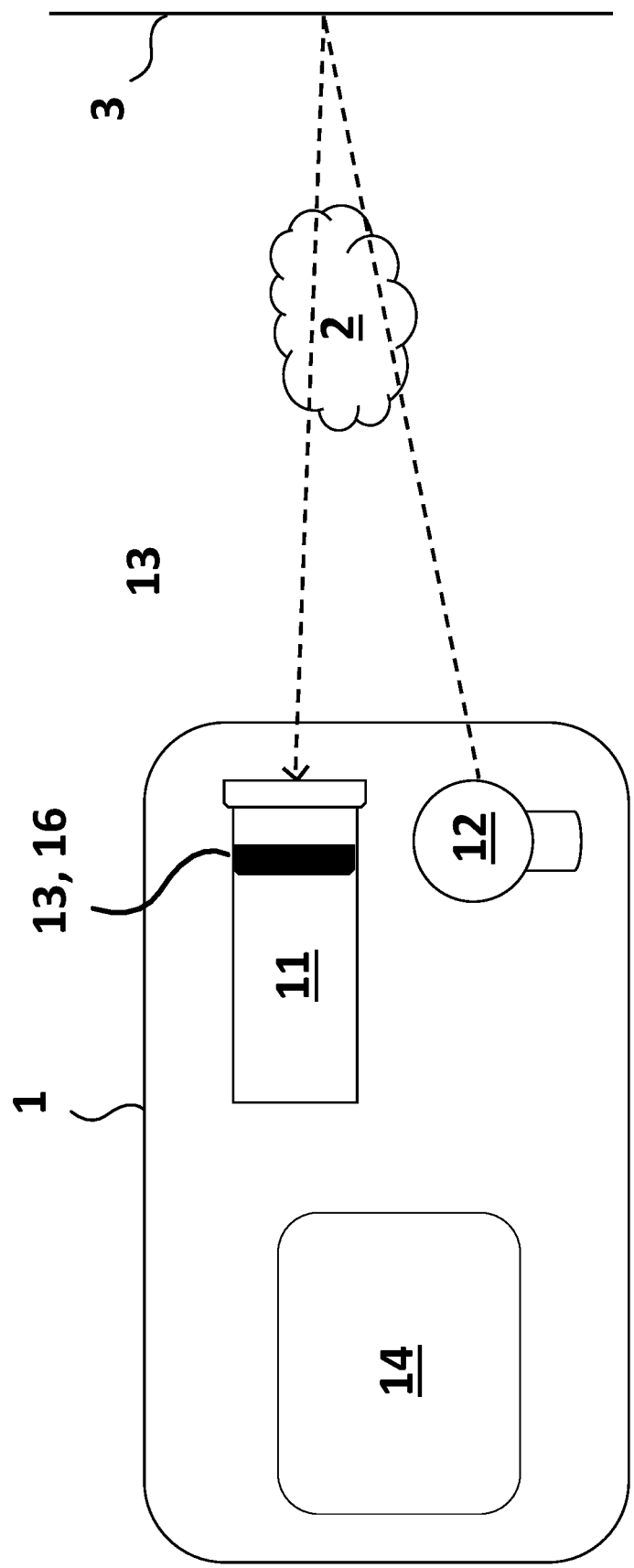
FIG. 1 shows a schematic illustration of a first exemplary embodiment of the device according to the present disclosure.

FIG. 1 shows a first exemplary embodiment of the device 1 according to the invention or of the method according to the invention.

The device 1 consists substantially of an optical capture unit 11—in the present case, a passive gas camera, i.e., an infrared camera with one or more optical filters 13, 13', which are in particular cooled. The optical capture unit 11 is expanded to include a first light source 12. The first light source 12 is a monochromatic light source, and in particular a laser or similar suitable light source. The first light source 12 is designed to emit light of a current wavelength, which current wavelength lies within a first, and in particular narrowband, wavelength range. The first light source is in particular tunable, i.e., the current wavelength can be shifted within the first wavelength range. Furthermore, a control/evaluation unit 14 is provided which controls the optical capture unit 11, i.e., can initiate video and image recordings, and can switch the first light source 12 on and off, and can set the current wavelength of the light emitted by the first light source 12.

The device is operated, in succession, first in a passive detection mode and subsequently in an active detection mode.

In the passive detection mode, the first light source 12 is switched off. The control/evaluation unit 14 instructs the optical capture unit 11 to record a first image of its field of view. A first optical filter is mounted in the optical capture unit 11, and in particular in a corresponding filter holder 16 of the optical capture unit 11, which optical filter 13 is arranged in the beam path of the incident light. The first optical filter is a bandpass filter which lets infrared light through only in the vicinity of the absorption lines of the sought gas 2. In the captured first image, gas 2 that may be present is thus optically separated from the background.

The first image is analyzed by the control/evaluation unit 14 or an external unit, e.g., a PC, by means of algorithms, e.g., image recognition algorithms, and the presence, and in particular the position, of the gas 2 is determined.

Since gas is frequently present as a mixture whose composition or concentration can be varied, the device 1 is subsequently operated in an active detection mode. For this purpose, the device is directed towards the gas or the gas mixture 2. The position of the gas 2 has been obtained from the analyzed first image. The gas or gas mixture to be analyzed is now located in the beam path of the emitted light and/or of the reflected light. For the active detection mode, the first light source 12 is switched on and set to a first current wavelength which lies outside the gas line of the gas or the gas mixture 2, i.e., is sufficiently distant from the wavelength at which the light emitted by the first light source 12 is maximally absorbed by the gas or the gas mixture 2. The light emitted by the first light source 12 leaves the device 1, is reflected on a background such that reflected light is captured by the optical capture unit. The control/evaluation unit 14 instructs the optical capture unit 11 to record a second image of its field of view.

The control/evaluation unit 14 instructs the optical capture unit 11 to record a third image of its field of view. For this purpose, the first light source 12 is set to a second current wavelength at which the light emitted by the first light source 12 is maximally absorbed by the gas or the gas mixture 2.

By analyzing the second and the third image, in particular by image differencing, the control/evaluation unit 14, or an external unit, can determine the composition of the gas or of the gas mixture, and/or identify the gas or the gas mixture 2. This is possible in that the current wavelength of the light emitted by the first light source is set such that it is located in the absorption spectrum of the gas 2.

For more accurate determination, further images can be recorded by the optical capture unit 11. The first light source is controlled in such a way that the current wavelength is shifted for each further image to be recorded. As a result, an absorption line of the gas is attained, on the basis of which the properties of the gas or of the gas mixture 2 can be determined precisely. The absorption line will look different for each gas mixture. The absorption line shows local minima at those wavelengths which correspond to the absorption wavelength of the corresponding gas component.

Advantageously, at a time at which the optical capture unit 11 is directed next to the gas 2, corresponding images for different current wavelengths of the light emitted by the first light source 12 are also to be sent out. This reference spectrum is used for the analysis of the gas or the gas mixture 2.

In order to be able to obtain plausible results, certain requirements of the optical filter 13 and the first light source 11 must be met. The spectral detection range must cover the selected absorption lines of the target gas. Furthermore, the current wavelength, or the first wavelength range, of the light emitted by the first light source must be detected by the optical capture unit 11. The first optical filter must therefore be selected such that it lets through light in the first wavelength range. In the event that the optical filter has a filter wavelength range in the middle infrared range, the first optical filter must be cooled in order to have as little thermal radiation from the first optical filter onto the detector of the optical capture unit 11 as possible. If the filter wavelength range is in the near-infrared range or in the ultraviolet range, cooling is not required. The current wavelength, or the first wavelength range, must also be selected such that it matches a unique absorption line of the target gas. In this case, no spectral overlap with another gas should take place, in order to enable a gas-specific detection.

The device according to the invention combines the advantages of active and passive gas detection. In one application example, the device 1 is part of a robot which is used in an industrial installation. In the passive detection mode, the optical capture unit 11 detects a gas cloud at a distance of 50 meters. The control/evaluation unit 14 identifies its position. However, the exact properties of the gas cannot yet be quantified on the basis of the passive detection mode alone. The robot approaches the detected position, wherein the device switches to the active detection mode. In this mode, the control/evaluation unit 14 confirms that it is escaping methane. For this purpose, a column concentration of 1,000 ppm*m is measured at a distance of 1 meter from the pipeline. If the optical path length cannot be isolated further, a minimum concentration of 500 ppm is transmitted (1,000 ppm*m/(2*1 m)). In the present example, an absorption maximum is established at 3.267 µm, as a result of which the device identifies the gas as methane by comparison with known values. Methane, in fact, has, for example, large absorption lines in the range of approximately 1.6 µm (near-infrared), 2.3 µm, and 3.3 µm (mid-infrared). By means of intelligent algorithms, the control/evaluation unit 14 can quantify escaping gas amount on the basis of the recorded images and, if necessary, also trace the leakage source (for example, in a pipeline or on a wall of a container). The active approach also functions when the gas cloud covers the entire image, whereas this would not be possible by means of passive detection.

Figure 2:
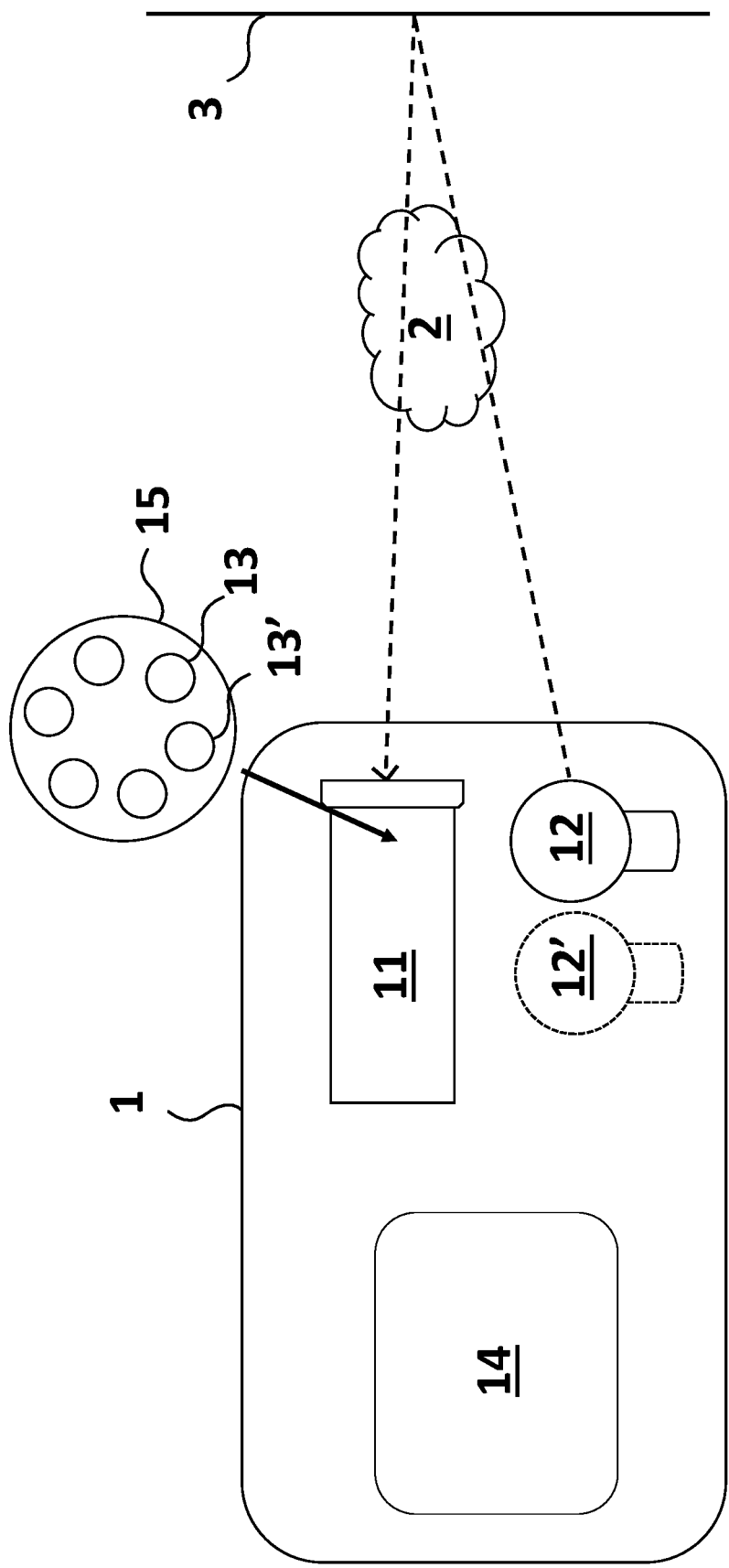
FIG. 2 shows a schematic illustration of a second exemplary embodiment of the device according to the present disclosure.

FIG. 2 shows a second exemplary embodiment of the device according to the invention. To detect different types of gas, the device has one or more further light sources 12', which can be switched on and off as desired by the control/evaluation unit. A further optical filter 13' is assigned to each of the further light sources 12'. Advantageously, the optical filters 13, 13' are arranged in a, preferably cooled, filter wheel 15 which, by rotating, easily arranges one of the filters 13, 13' in the beam path of the incident light in the optical capture unit 11.

The one or more of the further light sources can now be switched on successively, wherein in particular several current wavelengths are set one after another, and wherein the optical capture unit records one or more further current images, wherein the further image or the further images are also evaluated to determine the composition of the gas or the gas mixture (2), or to identify the gas or the gas mixture (2). As a result, a wide variety of gas mixtures having gas fractions with a wide variety of spectral properties can be analyzed and determined.

The invention claimed is:

1. A device for detection of a gas or of a multi-component gas mixture, the device comprising:
   an optical capture unit configured to record images of a field of view of the optical capture unit;
   a first light source configured to emit light at more than one wavelength, which can be set within a first wavelength range,
   wherein the first light source is configured to be selectively switched on and off, and
   wherein the first light source is arranged in relation to the optical capture unit such that the light emitted by the first light source impinges on the field of view of the optical capture unit;
   a first optical filter arranged in the field of view of the optical capture unit and between the optical capture unit and the first light source,
   wherein the first optical filter is configured to be selectively applied, and
   wherein the first optical filter enables only those wavelengths of the emitted light within a first filter wavelength range to pass therethrough,
   wherein the first wavelength range of the first light source is within the first filter wavelength range; and
   a control/evaluation unit configured to determine, based on at least one image recorded by the optical capture unit, at least one of:
      the presence of the gas or the gas mixture;
      the distribution of the gas or the gas mixture in the field of view of the optical capture unit;
      a composition of the gas or the gas mixture; and
      a concentration of the components of the gas mixture,
   wherein the control/evaluation unit is further configured to:
      operate the device in a passive detection mode, in which the first light source is switched off, and the optical capture unit captures a first image;
      evaluate the captured first image and determine the position of a gas or a gas mixture in the field of view of the optical capture unit;
      operate the device in an active detection mode, in which:
         the first light source is switched on and emits light within a first current wavelength;
         the device with the optical capture unit is directed toward the determined position and a second image is captured using the optical capture unit at the first current wavelength;
         the first light source emits a second current wavelength different from the first current wavelength; and
         a third image is captured at the second current wavelength at the determined position using the optical capture unit; and
      determine the composition of the gas or the gas mixture, or identify the gas or the gas mixture, by evaluating the second image and the third image.

2. The device of claim 1, wherein the control/evaluation unit is configured to synchronize a setting of at least one current wavelength of the first light source with a triggering of the optical capture unit to record the at least one image.

3. The device of claim 1, wherein the control/evaluation unit is configured to set the first light source sequentially to at least two current wavelengths that differ from one another,
   wherein the first light source is configured to trigger the optical capture unit when the first light source is set accordingly to the respective at least two current wavelengths.

4. The device of claim 1, wherein the device includes at least one further optical filter,
   wherein each of the at least one further optical filter has a further filter wave range different from one another and from the first filter wave range.

5. The device of claim 4, further comprising a filter wheel that includes the first optical filter and the at least one further optical filter, wherein the filter wheel is configured to selectively arrange the first optical filter, the at least one further optical filter or no optical filter in the field of view of the optical capture unit by rotating the filter wheel.

6. The device of claim 4, further comprising a filter holder configured to arrange the first optical filter and the at least one further optical filter in the field of view of the optical capture unit,
wherein the first optical filter, the at least one further optical filter or no optical filter can be selectively arranged in the filter holder.

7. The device of claim 1, wherein the first wavelength range of the first light source is narrowband.

8. The device of claim 1, wherein the first wavelength range is in the infrared range or in the UV range.

9. The device of claim 1, further comprising one or more further light sources,
wherein the further light sources each have a further wavelength range different from one another and from the first wavelength range,
wherein the further light sources are configured to be selectively switched on and off, and
wherein the further light sources are arranged relative to the optical capture unit such that emitted light from the further light sources impinges on the field of view of the optical capture unit.

10. The device of claim 9, wherein the further light sources are each a tunable laser diode or a tunable quantum cascade laser.

11. The device of claim 1, wherein the first light source is a tunable laser diode or a tunable quantum cascade laser.

12. The device of claim 1, further comprising an optical manipulation unit configured:
to widen the emitted light from the first light source such that the emitted light impinges on the field of view of the optical capture unit completely; or
such that the emitted light from the first light source is present in a punctiform manner and traverses the complete field of view in a raster pattern, wherein the control/evaluation unit is configured to record a plurality of images at different positions of the light in the raster.

13. The device of claim 12, further comprising one or more further light sources,
wherein the optical manipulation unit is configured:
as to widen the emitted light from the further light sources such that the emitted light impinges on the field of view of the optical capture unit completely; or
such that the emitted light from the further light sources is present in a punctiform manner and travels in a raster pattern over the field of view of the optical capture unit,
wherein the control/evaluation unit is configured to record a plurality of images at different positions of the light in the raster.

14. The device according to claim 1, wherein the first light source sequentially emits the first current wavelength and one or more further current wavelengths, wherein the optical capture unit records at least one further image when each of the further current wavelengths is present, and wherein the at least one further image is also evaluated to determine the composition of the gas or the gas mixture or to identify the gas or the gas mixture.

15. A method for detection of a gas or of a multi-component gas mixture using the device according to claim 1, the method comprising:

operating the device in a passive detection mode, wherein the first light source is switched off in the passive detection mode, and the optical capture unit captures a first image;
evaluating the captured first image and determining the position of a gas or a gas mixture in the field of view of the optical capture unit;
operating the device in an active detection mode, wherein the first light source is switched on in the active detection mode and emits light within the first current wavelength, the active detection mode further comprising:
aiming the device with the optical capture unit towards the determined position and capturing a second image using the optical capture unit; and
capturing a third image using the optical capture unit at the determined position, wherein the first light source emits a second current wavelength different from the first current wavelength; and
determining the composition of the gas or the gas mixture, or identifying the gas or the gas mixture, by evaluating the second image and the third image.

16. The method of claim 15,
wherein the first light source sequentially emits the first current wavelength and one or more further current wavelengths,
wherein the optical capture unit records at least one further image when each of the further current wavelengths is present, and
wherein the at least one further image is also evaluated to determine the composition of the gas or the gas mixture or to identify the gas or the gas mixture.

17. The method of claim 15,
wherein the device comprises one or more further light sources,
wherein the further light sources each have a further wavelength range different from one another and from the first wavelength range,
wherein the further light sources are configured to be selectively switched on and off, and
wherein the further light sources are arranged relative to the optical capture unit such that emitted light from the further light sources impinges on the field of view of the optical capture unit, the method further comprising:
subsequently switching on the one or more of the further light sources sequentially,
wherein further current wavelengths are set one after another, and
wherein the optical capture unit records one or more further current images,
wherein the further images are also evaluated to determine the composition of the gas or the gas mixture or to identify the gas or the gas mixture.

18. The method of claim 17,
wherein the device includes at least one further optical filter,
wherein each of the at least one further optical filter has a further filter wave range different from one another and from the first filter wave range, the method further comprising:
connecting one of the at least one further optical filters for each of the further light sources.

19. A device for detection of a gas or of a multi-component gas mixture, the device comprising:
an optical capture unit configured to record images of a field of view of the optical capture unit;

a first light source configured to emit light at more than one wavelength, which can be set within a first wavelength range,
wherein the first light source is configured to be selectively switched on and off, and
wherein the first light source is arranged in relation to the optical capture unit such that the light emitted by the first light source impinges on the field of view of the optical capture unit;
a first optical filter arranged in the field of view of the optical capture unit and between the optical capture unit and the first light source,
wherein the first optical filter is configured to be selectively applied, and
wherein the first optical filter enables only those wavelengths of the emitted light within a first filter wavelength range to pass therethrough,
wherein the first wavelength range of the first light source is within the first filter wavelength range; and
a control/evaluation unit configured to determine, based on at least one image recorded by the optical capture unit, at least one of:
the presence of the gas or the gas mixture;
the distribution of the gas or the gas mixture in the field of view of the optical capture unit;
a composition of the gas or the gas mixture; and
a concentration of the components of the gas mixture,
wherein the control/evaluation unit is further configured to:
set the first light source sequentially to at least two current wavelengths that differ from one another, wherein the first light source is configured to trigger the optical capture unit when the first light source is set accordingly to the respective at least two current wavelengths;
operate the device in a passive detection mode, in which the first light source is switched off, and the optical capture unit captures a first image;
evaluate the captured first image and determine the position of a gas or a gas mixture in the field of view of the optical capture unit;
operate the device in an active detection mode, in which:
the first light source is switched on and emits light within the first current wavelength;
the device with the optical capture unit is directed toward the determined position and a second image is captured using the optical capture unit at the first current wavelength;
the first light source emits a second current wavelength different from the first current wavelength; and
a third image is captured at the second current wavelength at the determined position using the optical capture unit; and
determine the composition of the gas or the gas mixture, or identify the gas or the gas mixture, by evaluating the second image and the third image.

* * * * *